United States Patent [19]

Yagi et al.

[11] Patent Number: 5,424,411
[45] Date of Patent: Jun. 13, 1995

[54] E. COLI-DERIVED UPSTREAM REGULATORY SEQUENCE OPERABLE IN YEAST

[75] Inventors: Shintaro Yagi; Kiyoko Tanaka; Juri Yoshioka; Masanori Suzuki, all of Saitama, Japan

[73] Assignee: Tonen Corporation, Tokyo, Japan

[21] Appl. No.: 751,304

[22] Filed: Aug. 28, 1991

[30] Foreign Application Priority Data

Aug. 30, 1990 [JP] Japan .................... 2-226566

[51] Int. Cl.⁶ .............................. C12N 15/11
[52] U.S. Cl. .................... 536/24.1; 435/69.1; 435/254.21; 935/36; 935/37
[58] Field of Search ............... 435/69.1, 172.3, 320.1; 935/33, 37, 41, 27; 536/27, 23.1, 24.1

[56] References Cited

U.S. PATENT DOCUMENTS 4,833,080  5/1989  Brent et al. .............. 435/172.3
5,089,398  2/1992  Rosenberg et al. ......... 435/69.1

FOREIGN PATENT DOCUMENTS 164556  12/1985  European Pat. Off. ..... C12N 15/00
248410  12/1987  European Pat. Off. ..... C12N 15/00

OTHER PUBLICATIONS

Kwak et al., "A Method to Isolate DNA Sequences that are Promoter Active in *Escherichia coli* and in yeast," Biochem. Biophy. Res. Comm. 149(3):846–851 (Dec. 1987).

Goodley et al., "The Selection of Promoters for the Expression of Heterologous Genes in the Yeast *Saccharomyces cerevisiae*," Mol. Gen. Genet. 204:505–511 (1986).

Sidhu et al., *Yeast*, vol. 6, No. 3, 1990, pp. 221–229.

Ciaramella et al., *Nucleic Acids Research*, vol. 16, No. 18, 1988, pp. 8846–8868.

*Primary Examiner*—Richard A. Schwartz
*Assistant Examiner*—James Ketter
*Attorney, Agent, or Firm*—Wegner, Cantor, Mueller & Player

[57] ABSTRACT

A hybrid upstream regulatory sequence including an upstream regulatory sequence of *E. coli* origin and yeast upstream regulatory sequence, which hybrid upstream regulatory sequence can function in a yeast cell; a hybrid promoter including the regulatory sequence of *E. coli* origin and a TATA region of a yeast promoter, which hybrid promoter can also function in a yeast cell; a hybrid promoter including the upstream regulatory sequence of *E. coli* origin and a yeast promoter, which hybrid promoter can function in a yeast cell; and a plasmid useful for a test of an upstream regulatory sequence, including a TATA region of a yeast promoter, a structural gene containing a translation start codon, and a yeast origin of replication.

4 Claims, 15 Drawing Sheets

SN1-10

```
            10           20           30
      AA|GATCT|GGT TCAAATAATT CACTTTCAAA
            40           50           60
      TGAATGCGTC AGTGGTGGCA AACGCATCAG
            70           80           90
      |GATC|TTTTAA CGAAATGTTA ACTATC|GATC|
           100          110          120
      GCCGTGCAGT TTCATGATTT CCTGGCCCGG
           130          140          150
      GCGCAGCACA GGTGGAAGGT GTTGCCGAGG
           160          170          180
      ATAATTTGCG CGCCAGTGGC TTCAACTTGT
           190          200          210
      TCGCGCGTCA TCCCTTTTAC GGTGCCGTAG
           220          230          240
      GTGCCAACAG GCATAAAACA AGGCGTTTCC
           250         255
      ACTACGCCAC |GATCT|
```

→ START OF ACTIVE FRAGMENT

└→ Sau3AI SITE

AA|GATC|TGGT TCAAATAATT CACTTTCAAA

TGAATGCGTC AGTGGTGGCA AACGCATCAG

|GATC|TTTTAA CGAAATGTTA ACTATC|GATC| →90

GCCGTGCAGT TTCATGATTT CCTGGCCCGG

GCGCAGCACA GGTGGAAGGT GTTGCCGAGG

ATAATTTGCG CGCCAGTGGC TTCAACTTGT

TCGCGCGTCA TCCCTTTTAC GGTGCCGTAG

GTGCCAACAG GCATAAAACA AGGCGTTTCC

ACTACGCCAC |GATC|T

→ START OF ACTIVE FRAGMENT

└⊐ Sau3AI SITE

```
         10          20          30
AAGATCTGCG  CCCCGCAGTG  AGTTGCTGAT
         40          50          60
ACCAGCGTTG  CAGATTTGGA  CGCGGTGTCC
         70          80          90
AGGTCAGGCC  GGCCAGACGC  TGCCTTCTCT
        100         110         120
GTTGCACGGC  GATTTATGGT  CCGGCAACTG
        130         140         150
TGCACTGGGT  CCGGATGGCC  CGTACACAGA
153
TCT
```

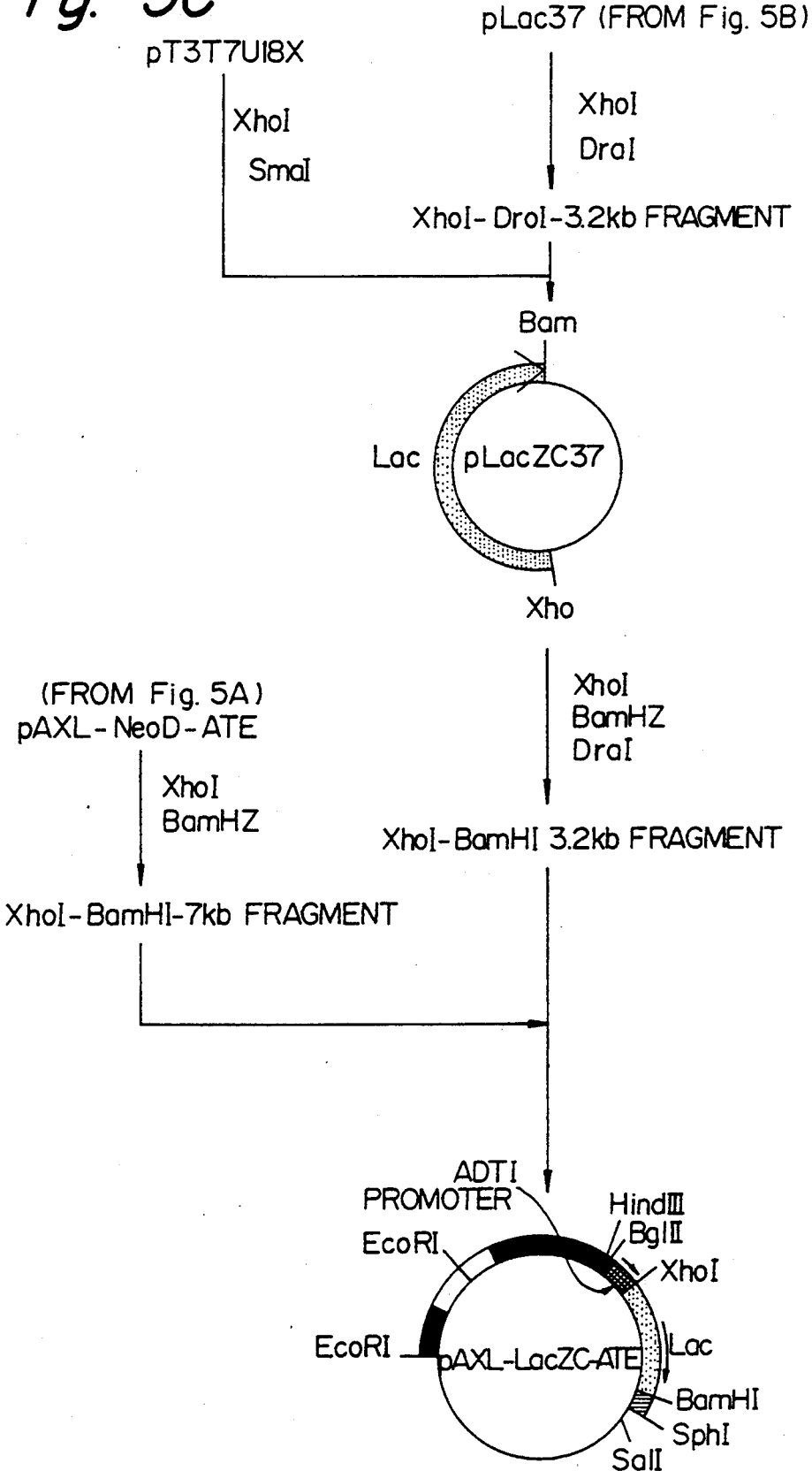

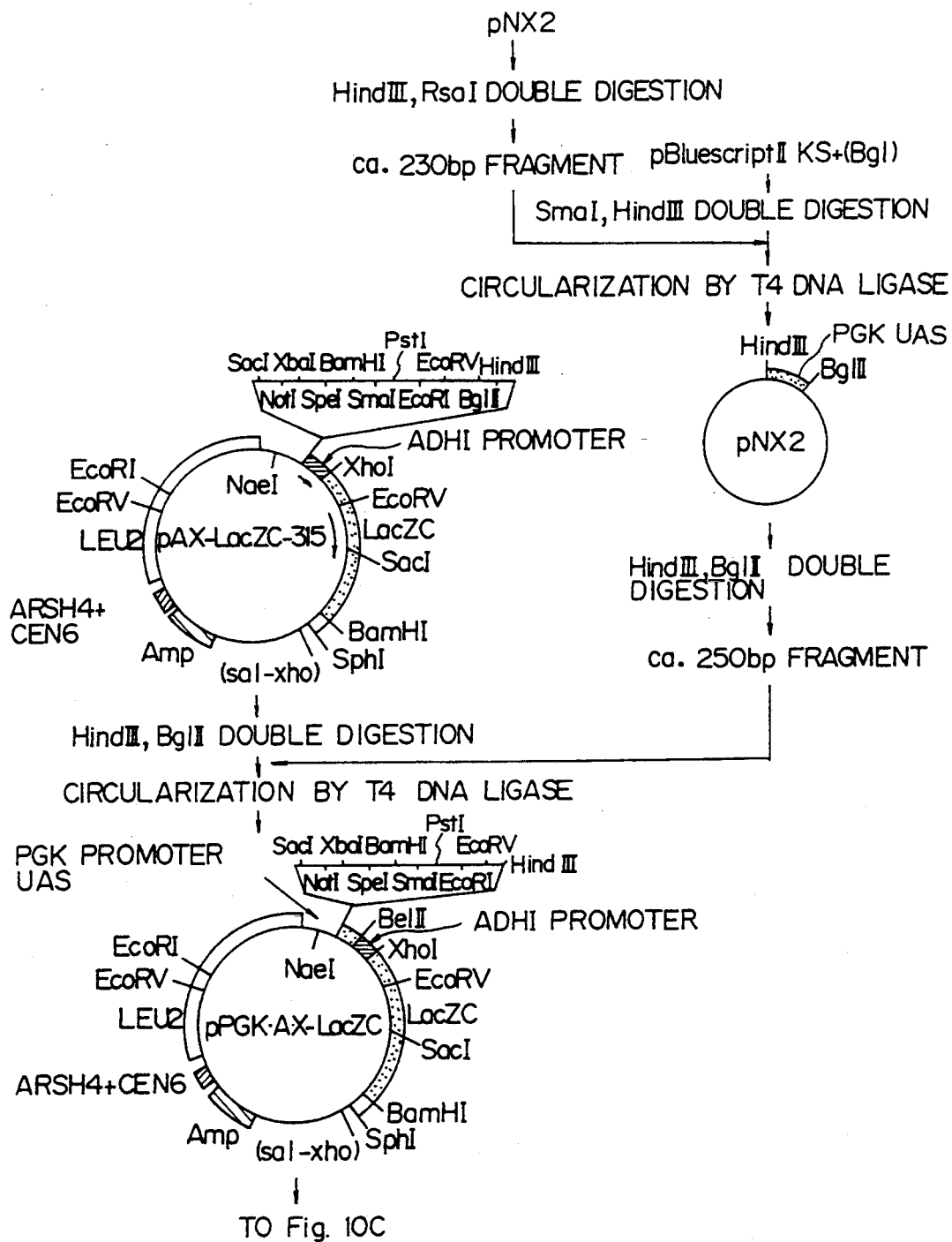

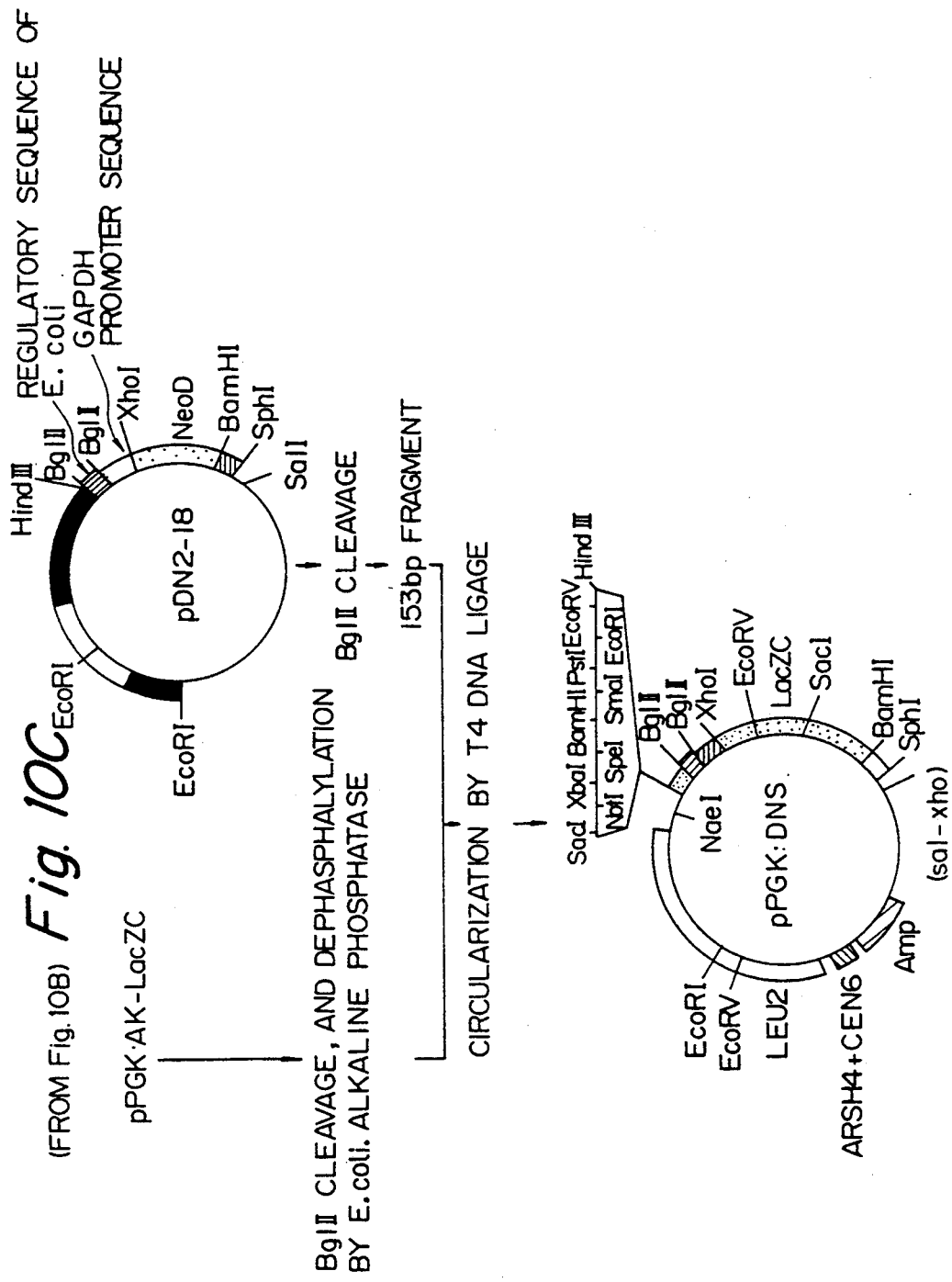

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 255 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:1:

```
AAGATCTGGT TCAAATAATT CACTTTCAAA TGAATGCGTC AGTGGTGGCA AACGCATCAG      60
GATCTTTTAA CGAAATGTTA ACTATCGATC GCCGTGCAGT TTCATGATTT CCTGGCCCGG     120
GCGCAGCACA GGTGGAAGGT GTTGCCGAGG ATAATTTGCG CGCCAGTGGC TTCAACTTGT     180
TCGCGCGTCA TCCCTTTTAC GGTGCCGTAG GTGCCAACAG GCATAAAACA AGGCGTTTCC     240
ACTACGCCAC GATCT                                                      255
```

( 2 ) INFORMATION FOR SEQ ID NO:2:

( i ) SEQUENCE CHARACTERISTICS:
        ( A ) LENGTH: 153 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:2:

```
AAGATCTGCG CCCCGCAGTG AGTTGCTGAT ACCAGCGTTG CAGATTTGGA CGCGGTGTCC      60
AGGTCAGGCC GGCCAGACGC TGCCTTCTCT GTTGCACGGC GATTTATGGT CCGGCAACTG     120
TGCACTGGGT CCGGATGGCC CGTACACAGA TCT                                  153
```

( 2 ) INFORMATION FOR SEQ ID NO:3:

( i ) SEQUENCE CHARACTERISTICS:
        ( A ) LENGTH: 21 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:3:

```
TAGCCTCTGC ACCCAAGCGG C                                                21
```

( 2 ) INFORMATION FOR SEQ ID NO:4:

( i ) SEQUENCE CHARACTERISTICS:

(A) LENGTH: 36 base pairs
    (B) TYPE: nucleic acid
    (C) STRANDEDNESS: double
    (D) TOPOLOGY: linear (ii) MOLECULE TYPE: DNA (genomic)

(xi) SEQUENCE DESCRIPTION: SEQ ID NO:4:

AGCTTGATAT CAAGATCTAC TATAGTTCTA GATCGA                                36

(2) INFORMATION FOR SEQ ID NO:5:

(i) SEQUENCE CHARACTERISTICS:
    (A) LENGTH: 40 base pairs
    (B) TYPE: nucleic acid
    (C) STRANDEDNESS: double
    (D) TOPOLOGY: linear (ii) MOLECULE TYPE: DNA (genomic)

(xi) SEQUENCE DESCRIPTION: SEQ ID NO:5:

AATTGCTCGA GATGGATATC CGAGCTCTAC CTATAGCTAG                            40

(2) INFORMATION FOR SEQ ID NO:6:

(i) SEQUENCE CHARACTERISTICS:
    (A) LENGTH: 30 base pairs
    (B) TYPE: nucleic acid
    (C) STRANDEDNESS: double
    (D) TOPOLOGY: linear (ii) MOLECULE TYPE: DNA (genomic)

(xi) SEQUENCE DESCRIPTION: SEQ ID NO:6:

GTCCAAGATT TGGACTTGAA GGACAAGCGT                                       30

(2) INFORMATION FOR SEQ ID NO:7:

(i) SEQUENCE CHARACTERISTICS:
    (A) LENGTH: 12 base pairs
    (B) TYPE: nucleic acid
    (C) STRANDEDNESS: double
    (D) TOPOLOGY: linear (ii) MOLECULE TYPE: DNA (genomic)

(xi) SEQUENCE DESCRIPTION: SEQ ID NO:7:

AATTGCTCGA GC                                                          12

E. COLI-DERIVED UPSTREAM REGULATORY SEQUENCE OPERABLE IN YEAST

BACKGROUND OF THE INVENTION

1. Field of the Invention

The present invention relates to an E. coli-derived upstream regulatory sequence operable in yeast.

2. Description of the Related Art

Recently, information useful for genetic engineering has been rapidly accumulated for yeast as well as E. coli. In addition, yeast is widely used as a host for the production of substances by genetic engineering, because there is much knowhow relating to its fermentation. To express gene coding for a substance to be produced in yeast cells, generally, a powerful promoter of yeast origin is used. The reason is that efficient transcription of a gene is essential for efficient production of a substance. Therefore, promoters of genes for glycolytic enzymes such as phosphoglucokinase (PGK), glyceraldehyde-3-phosphate dehydrogenase (GAPDH), and the like are used. Where a repressible promoter is preferred due to the instability of the heterogeneous gene product in yeast cells or toxicity of the product, a promoter GAL1, PHO5, CUP1, ADH2, or the like is used.

It is known that these promoters comprise at least two functionally different regions. One is a region comprising a so-called TATA sequence and a transcription start point (hereinafter designated as "TATA region"), and another is an upstream regulatory sequence (URS) present upstream of the TATA region. Generally, a URS includes an upstream activating sequence (UAS) and an upstream inhibitory sequence (UIS). In yeast, synthesis of a gene product is controlled by controlling the transcription by a combination of these sequences. Moreover, it is known that a URS can function in a combination with a TATA region, different from a combination with a native TATA, and that the functions of UAS and UIS do not depend on the direction relative to the TATA region. Moreover, it is considered that the activity of a promoter reflects the activity of UAS. It is believed that this type of control necessarily applies to expression of a foreign gene.

From the above, it is expected that novel promoters capable of efficient expression of a foreign gene can be developed by a combination of URS's of different genes or a combination of a URS and a TATA region of different genes. According to such a strategy, Bitter et al., Gene, 69, pp 193–207, 1988, reported that they developed a hybrid promoter which can be controlled by galactose and has a transcriptional activity higher than that of a GAL1 promoter and also developed an efficient expression system for interferon production. In similar attempts, there have been reported a hybrid promoter comprising a combination of a control region of ADH2 and a promoter of GAPDH, which hybrid promoter can be controlled by ethanol and has a transcriptional activity higher than that of an ADH2 promoter (Cousen et al., Gene, 61, pp 265–275, 1987); a hybrid promoter comprising a combination of a control region of a PHO5 and GAPDH promoter, which hybrid promoter can be controlled by a phosphate concentration in a culture medium and has a transcriptional activity higher than that of a PHO5 promoter (Hinnen et al., Yeast Genetic Engineering, BuHerworth, 1989), and the like. However, although the GAPDH promoter used above contains a UAS of GAPDH, the activities of the above-mentioned hybrid promoters are not greater than those of GAPDH.

As seen from the above, although it is believed that the most powerful promoters in yeast are those of genes for glycolytic enzymes, there have not been reported promoters much more active than native promoters.

SUMMARY OF THE INVENTION

Accordingly, the present invention provides upstream regulatory sequences providing an activity higher than those of native promoters, in combination of promoter of gene for a glycolytic enzyme, and yeast expression systems comprising novel upstream regulatory sequences to improve the expression of a foreign gene and the production of the gene product.

More particularly, the present invention provides an isolated upstream regulatory sequence, derived from E. coli, which can function in a yeast cell.

The present invention also provides a hybrid upstream regulatory sequence comprising the above-mentioned upstream regulatory sequence of E. coli origin and yeast upstream regulatory sequence, which hybrid upstream regulatory sequence can function in a yeast cell.

The present invention moreover provides a hybrid promoter comprising the above-mentioned upstream regulatory sequence of E. coli origin and a TATA region of a yeast promoter, which hybrid promoter can function in a yeast cell.

The present invention further provides a hybrid promoter comprising the above-mentioned upstream regulatory sequence of E. coli origin and a yeast promoter, which hybrid promoter can function in a yeast cell.

The present invention still more provides a plasmid useful for a test of an upstream regulatory sequence, comprising a TATA region of a yeast promoter, a structural gene containing a translation start codon, and a yeast origin of replication.

Present invention further provides a process for production of a peptide comprising the steps of:
(1) culturing a yeast host transformed with an expression vector comprising a gene coding for an amino acid sequence of the peptide under the control of a hybrid upstream regulatory sequence comprising an upstream regulatory sequence derived from E. coli and yeast upstream regulatory sequence and
(2) recovering the expressed peptide.

The present invention moreover provides a process for production of a peptide comprising the steps of:
(1) culturing a yeast host transformed with an expression vector comprising a gene coding for an amino acid sequence of the peptide under the control of a hybrid promoter comprising a TATA region of a yeast promoter and an upstream regulatory sequence derived from E. coli and
(2) recovering the expressed peptide.

The present invention still more provides a process for production of a peptide comprising the steps of:
(1) culturing a yeast host transformed with an expression vector comprising a gene coding for an amino acid sequence of the peptide under the control of a hybrid promoter comprising a yeast promoter and an upstream regulatory sequence derived from E. coli and
(2) recovering the expressed peptide.

BRIEF DESCRIPTION OF THE DRAWINGS

FIG. 3 shows a nucleotide sequence SEQ ID NO: 1 of a DNA fragment SN1-10 containing an upstream regulatory sequence of the *E. coli* chromosome, wherein a nucleotide sequence from the 87th G to the 250th C exhibits an upstream activating action;

FIG. 4 shows a nucleotide sequence (SEQ ID NO:2) of an upstream regulatory (activating) sequence DN2-18 derived from the *E. coli* chromosome;

FIGS. 5A, 5B, and 5C show a process for construction of a plasmid pAXL-LacZC-ATE for a test of an upstream regulatory sequence;

FIGS. 10A to 10C show a process for construction of plasmid pPGK-DNS; and

DESCRIPTION OF THE PREFERRED EMBODIMENTS

To screen unknown regulatory sequences and to test their functions, the following conditions should be satisfied. First, since a yeast promoter contains its intrinsic upstream regulatory sequence, to test a foreign upstream regulatory sequence, a promoter from which the intrinsic upstream regulatory sequence has been deleted should be prepared. For example, regulatory sequences of GAL1-GAL10 may be tested by combining the regulatory sequences with a promoter of CYC1 from which the upstream regulatory sequence has been deleted.

Moreover, for a simple test, a sequence to be tested should be inserted upstream of a gene whose expression can be relatively simply and quantitatively measured. As an example of such a gene, β-galactosidase gene (LacZ) has been often used.

In addition, to insert a sequence to be tested into a test plasmid by gene manipulation using an *E. coli* host, and to carry out the test in yeast cells, the plasmid should be a shuttle vector which can replicate in both the *E. coli* cells and yeast cells.

Figure 1:
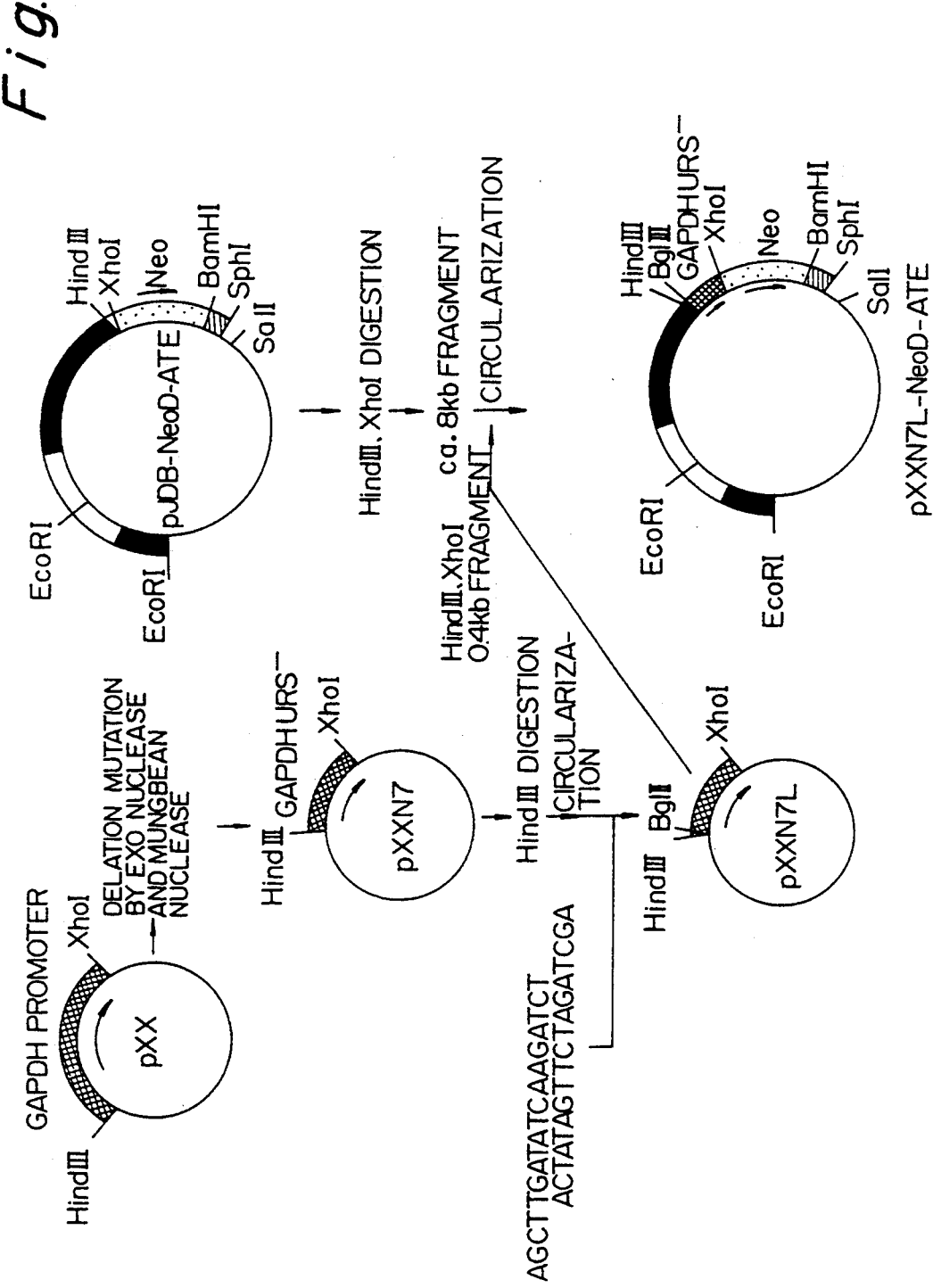
FIG. 1 shows a process for construction of a plasmid pXXLN7-NeoD-ATE for a test of the upstream regulatory sequence.

As plasmids which satisfy the above-mentioned requirements, in the present invention, use is made of a test system using the Neogene described in Japanese Unexamined Patent Publication (Kokai) No. 2-222689. Relatively powerful promoter sequences can be tested by using a NeoD gene in which ATG codons present upstream of the ATG translation start codon have been deleted, leaving only one ATG codon. Note it has been known that the NeoD gene provides a neomycin resistance to yeast only when it is expressed under a powerful promoter. Therefore, according to the present invention, a promoter sequence prepared by deleting the native upstream regulatory sequence from the GAPDH gene promoter is prepared, and the promoter sequence thus prepared is inserted into pJDB-NeoD-ATE having a NeoD gene to construct a test plasmid pXXN7L-DeoD-ATE. The test plasmid can be used for simply screening and testing upstream regulatory sequences by observing the level of G418 resistance. An example of the construction process is shown in Example 1 and FIG. 1.

Since the plasmid pXXN7L-NeoD-ATE has HindIII and BglII sites upstream of the GAPDH promoter fragment, a sequence to be tested can be easily inserted into the test plasmid using these sites. Yeast cells transformed with this plasmid do not exhibit G418 resistance at a concentration as low as 0.25 mg/ml.

The present invention provides an upstream regulatory sequence of *E. coli* origin which can function in yeast cells. The present upstream regulatory sequence is derived from *E. coli* chromosomal DNA. To obtain fragments containing an upstream regulatory sequence from *E. coli* chromosome DNA, the chromosomal DNA is preferably digested with a restriction enzyme whose recognizing sequence is short or cut with ultrasonication. In the present invention, for example, DNA fragments are obtained by non-specific cleavage of the chromosomal DNA with DNase I in the presence of manganese ions or by complete digestion with a restriction enzyme Sau3AI whose recognizing sequence is 4 base pairs in length. Example 2 describes a method for cleavage of the chromosomal DNA, and Example 3 describes a screening method for the randomly cleaved DNA fragments of Example 2 to select an upstream regulatory sequence.

The present upstream regulatory sequence is novel. The sequencing method of the upstream regulatory sequence is described in Example 4. The fact that the present upstream regulatory sequence is different from those known in yeast is confirmed in that the present upstream regulatory sequence needs a length of as long as about 150 bp for its functions, and sequences similar to the present upstream regulatory sequence are not found in yeast gene banks.

On the other hand, the present regulatory sequence has functional properties similar to yeast upstream regulatory sequences. Namely, the present regulatory sequence functions in combination with any promoter, and the orientation relating to a promoter is not critical. These properties are described in Example 5.

The present invention also provides a hybrid promoter comprising an *E. coli* upstream regulatory sequence and a yeast promoter. For example, Example 5 shows that *E. coli*-derived upstream regulatory sequences of the present invention function in combination with a yeast ADHI promoter, and the regulatory sequences function in any orientation relating to the promoter. Yeast promoters which can function in combination with an upstream regulatory sequence of the present invention include a GAPDH promoter, PGK promoter, PYK promoter, and ENO1 promoter, in addition to the above-mentioned ADHI promoter.

The present invention also provides a hybrid promoter comprising an E. coli upstream regulatory sequence of the present invention and a TATA region of a yeast promoter. In this case, as TATA regions, TATA regions of a GAPDH promoter, PGK promoter, alcohol dehydrogenase I (ADHI) promoter, pyruvate kinase (PYK) promoter, enolase 1 (ENO1) promoter, triosephosphate isomerose (TPI) promoter, and the like may be mentioned. The effectiveness of this type of hybrid promoters is described in Example 3, wherein an E. coli derived upstream regulatory sequence prepared in Example 2, when inserted into an upstream regulatory test plasmid prepared in Example 1, provides an efficient expression of a Neo gene.

The present invention moreover provides a hybrid regulatory sequence comprising an E. coli-derived upstream regulatory sequence of the present invention and a yeast upstream regulatory sequence. The upstream regulatory sequences of the present invention exhibit the most effective functions when they are combined with a yeast regulatory sequence. When an upstream regulatory sequence of a PGK gene, one of the most powerful regulatory sequences in a yeast gene, is combined with an upstream regulatory sequence of the present invention, the function of the yeast regulatory sequence is further strengthened. This is clear from the experiment described in Example 6. It is found, in Example 6, that the above-mentioned upstream regulatory function is exhibited in centromere plasmids. The upstream regulatory sequence which forms a hybrid upstream regulatory sequence in combination with an E. coli upstream regulatory sequence of the present invention includes, in addition to the above-mentioned upstream regulatory sequence of a PGK promoter, upstream regulatory sequences of an ADH1 promoter, GAPDH promoter, ENO1 promoter, PYK promoter, and the like.

The upstream regulatory sequence, hybrid upstream regulatory sequence, and hybrid promoter of the present invention can be effectively used to express foreign genes. For example, upstream regulatory sequences of the present invention, such as SN1-10 and DN2-18, when combined with a GAPDH promoter fragment, exhibit an activity higher than that of a native GAPDH promoter. As an example of the use of these regulatory sequences to produce a large amount of a foreign gene product, the production of human serum albumin is described in Example 7. In this case, it is confirmed that not only where the regulatory sequence is maintained as a plasmid, but also where the regulatory sequence is incorporated into the yeast chromosome, the regulatory sequence exhibits its function.

The present invention further provides a plasmid for the test of the upstream regulatory sequence. The test plasmid has a TATA region of a yeast promoter and a structural gene with a translation start codon and can be used to test activity of a sequence to be tested by inserting the sequence upstream of the TATA region. In this case, various fragments having different activities can be tested by preparing a plurality of test plasmids having different structures upstream of the translation start codon and therefore have different potential abilities to express an inserted structural gene. The test plasmid is preferably a shuttle vector comprising an origin of replication and a selective maker for yeast, as well as an origin of replication and a selective maker for E. coli for manipulation of plasmid using E. coli cells. As the above-mentioned TATA regions, for example, TATA regions of a GAPDH promoter, PGK promoter, ADHI promoter PYK promoter, ENO1 promoter, TB1 promoter, and the like may be used, and as the above-mentioned structural genes, those whose expression products can be easily measured, such as a neomycin resistance gene, $\beta$-galactosidase gene, chroramphenycol, acetyl transferase, or the like may be used.

According to the present invention, the present upstream regulatory sequence of E. coli origin can be used to obtain very powerful hybrid promoter sequences. The hybrid promoter can provide a large amount of foreign gene products in yeast, not only where it is introduced into a plasmid of 2 $\mu$m origin or into a plasmid comprising a centromere sequence as an origin of replication, but also where it is introduced into the chromosome. For example, a large amount of human serum albumin can be produced.

Moreover, the upstream regulatory sequence of the present invention can be used in combination with an upstream regulatory sequence of a gene other than a gene for glycolytic enzymes. For example, the present upstream regulatory gene is used in combination with an upstream sequence of GAL1 to prepare an expression system which can be controlled by the addition of galactose. Moreover, the present regulatory sequence can be used in a combination with an upstream regulatory sequence of, for example, PHO5, CUP1, ADH2, and the like to construct high expression systems which can be regulated according to corresponding regulation mechanisms.

The present invention further provides a process for production of a peptide comprising the steps of:
(1) culturing a yeast host transformed with an expression vector comprising a gene coding for an amino acid sequence of the peptide under the control of a hybrid upstream regulatory sequence comprising an upstream regulatory sequence derived from E. coli and yeast upstream regulatory sequence and
(2) recovering the expressed peptide.

The present invention further provides a process for production of a peptide comprising the steps of:
(1) culturing a yeast host transformed with an expression vector comprising a gene coding for an amino acid sequence of the peptide under the control of a hybrid promoter comprising a TATA region of yeast promoter and an upstream regulatory sequence derived from E. coli and
(2) recovering the expressed peptide.

The present invention still more provides a process for production of a peptide comprising the steps of:
(1) culturing a yeast host transformed with an expression vector comprising a gene coding for an amino acid sequence of the peptide under the control of a hybrid promoter comprising a yeast promoter and an upstream regulatory sequence derived from E. coli and
(2) recovering the expressed peptide.

The present invention will now be described in detail with reference to the following examples.

The procedures commonly used in the examples are as follows.

1) Deletion Mutation Using ExoIII Nuclease and Mungbean Nuclease

5 $\mu$g of a plasmid was digested with an appropriate restriction enzyme, and the digestion product was extracted with phenol/chloroform and precipitated with ethanol to recover DNA. The DNA was dissolved in 50 $\mu$l of ExoIII buffer (50 mM Tris-HCl, pH 8.0, 100 mM NaCl 5 mMMgCl$_2$ and 10 mM 2-mercaptoethanol). To the DNA solution was added 180 units of ExoIII nuclease, the mixture was incubated at 37° C., and 5 μl of samples were taken at 30-second intervals from the addition of the enzyme.

The sample was transferred to 50 μl of MB buffer (40 mM sodium acetate, pH 4.5, 100 mM NaCl, 2 mM ZnCl$_2$ and 10% glycerol) cooled in ice. After finishing the sampling, the ice cooled mixture was heated to 65° C., incubated for 5 minutes at this temperature, and cooled to 37° C. 50 units of mungbean nuclease was added to the reaction mixture, which was then incubated at 37° C. for 30 minutes. After the reaction, the solution was extracted with phenol saturated with TE, and DNA was recovered by ethanol precipitation.

2) Restriction Enzyme Treatment

A restriction enzyme treatment was carried out according to reaction conditions recommended by the manufacturer of the enzyme.

3) T4 DNA Ligase Treatment

For example, 100 ng of a fragment and 20 ng of a fragment containing *E. coli* origin of replication were mixed to make 10 μl of a reaction mixture (50 mM Tris-HCl, pH 7.5, 10 mMMgCl$_2$, 10 mM DTT, 1 mM ATP), and 350 units of T4 DNA ligase was added to the reaction mixture, which was then incubated at 16° C. for 1 hour to overnight.

4) Medium Composition

*E. coli* cells were cultured in L medium (1% trypton, 0.5% yeast extract, and 0.5% sodium chloride). If necessary, ampicillin was added to a concentration of 50 μg/ml. For an agar medium, agar was added to a concentration of 1.5%.

For culturing yeast cells, a YPD medium was composed of 2% polypepton, 1% yeast extract, and 2% glucose; and for the agar medium, agar was additionally added to a concentration of 2%. Leucine-free SD medium contained 20 μg/ml adenine sulfate, 20 μg/ml arginine hydrochloride, 20 μg/ml methionine, 20 μg/ml histidine hydrochloride, 20 μg/ml tryptophan, 20 μg/ml uracil, 30 μg/ml isoleucine, 30 μg/ml lysine hydrochloride, 30 μg/ml tyrosine, 50 μg/ml phenylalanine, 150 μg/ml valine, 0.15% amino acid-free Yeast Nitrogen Base, 0.5% ammonium chloride, and 2% glucose. For an agar medium, agar was added to a concentration of 2%.

5) Preparation of RNA and Northern Hybridization

A colony was inoculated in 5 ml of SD medium and cultured at 30° C. for 2 days with shaking. A part of the culture (containing 2×10$^7$ cells) was inoculated to 50 ml of SD medium and cultured at 30° C. for 24 hours. 20 ml of this culture broth was centrifuged at 3000 rpm for 5 minutes to collect cells. The cells were re-suspended in 1 ml of 1M sorbitol, and the suspension was again centrifuged at 3000 rpm for 5 minutes to collect the cells. The cells were re-suspended in 1 ml of solution containing 400 μg/ml zymolyase and 1 M sorbitol, and after allowing the suspension to stand at 30° C. for 30 minutes, the suspension was centrifuged at 7000 rpm for 5 minutes to collect spheroplasts. The spheroplasts were re-suspended in 750 μl of TLES solution (Tris-HCl, pH 7.5, 0.1 M LiCl, 10 mM EDTA, and 1% SDS), 300 μl of TLE (Tris-HCl, pH7.5, 0.1 M LiCl, 10 mM EDTA)-saturated phenol was added thereon, and the whole was subjected to vortex-mixing.

Next, the suspension was centrifuged at 15,000 rpm for 10 minutes. The resulting aqueous layer was twice extracted with TLE-saturated phenol. To 600 μl of the resulting aqueous solution was added 200 μl of 8 M LiCl. After mixing, the mixture was allowed to stand at 4° C. overnight. The mixture was centrifuged at 15,000 rpm for 10 minutes to recover an RNA precipitate, which was then dissolved in 300 μl of sterilized water, 30 μl of 3 M sodium acetate solution (pH 5.2) was added thereon, followed by 750 μl of ethanol, and the mixture was allowed to stand at −80° C. for 2 hours. The mixture was centrifuged at 75,000 rpm for 10 minutes to recover an RNA precipitate, which was then washed with 70% ethanol and dried under a reduced pressure. The dried precipitate was dissolved in an appropriate amount of water to prepare an RNA sample.

2 μg of RNA was adjusted to a composition of 50% formamide, 2 M formaldehyde, and 1×MOPS buffer (10×MOPS buffer=0.2 M MOPS, 0.05 M sodium acetate and 0.01 M EDTA, adjusted to pH 7.0 with NaOH), and after incubating at 65° C. for 5 minutes, 0.1 volume of 0.01% bromophenol blue solution in 50% glycerol was added to the mixture, which was then separated by 1.1% agarose gel (1×MOPS buffer, 2 M formaldehyde) electrophoresis. After the electrophoresis, the RNA was transferred to a Hybond-N ™ filter (Amersham Japan) according to a recommendation by the manufacturer, and the RNA was fixed on the filter by UV irradiation.

This filter was put into a hybridization solution containing 50% formamide, and after incubating at 42° C. for 2 hours, transferred to the same solution containing a 1×10$^6$ cpm/ml probe, and incubated at 42° C. overnight. Note the probe was prepared by labeling a part of the structural gene of yeast phosphoglyceratekinase (PGK) with α-$^{32}$P-dCTP by a random priming method. The filter was washed with 0.1×SSC and 0.1% SDS at 60° C., and the remaining radioactivity was detected by exposing an X-AR film.

The filter, used for the detection, was transferred into a probe-removing solution (50 mM Tris-HCl, pH 7.5, 5×Denhalt's solution, 0.5% SDS, 100 μl/ml heat-denaturated salmon sperm DNA and 50% formamide), and incubated at 80° C. for 15 minutes. After repeating the same procedure, the filter was transferred to a hybridization solution. After incubating at 42° C. for 2 hours, the filter was transferred to the same solution containing a probe at concentration of 1×10$^6$ cpm/ml, and incubated at 42° C. overnight. Note, the probe was prepared by chemically synthesizing an oligonucleotide (5'-TAGCCTCTGCACCCAAGCGGC SEQ. ID. NO. 3) complementary to mRNA of a neomycin resistant gene and labeling the oligonucleotide at its 5'-terminus with γ-$^{32}$P-ATP and T4 polynucleotidekinase. The filter was washed with 2×SSC and 0.1% SDS at 60° C., and the remaining radioactivity was detected by exposing an X-AR film.

EXAMPLE 1

Construction of Improved Plasmid pXXN7L-NeoD-ATE for Test of Upstream Regulatory Sequence Plasmid pXX containing a GAPDH promoter was digested with XbaI and SphI, and the digestion was subjected to a deletion mutation using ExoIII nuclease and mungbean nuclease. Note, the construction process of the plasmid pXX is described in Japanese Patent Application No. 1-328264. The deletion-mutated plasmid was circularized with T4 DNA ligase and used to transform *E. coli* XL1-blue. The resulting ampicillin resistant colonies were tested and colonies having deletion-mutated plasmid were selected. A single-stranded DNA was prepared from each colony and sequenced using a Sequenase sequencing kit (UBS Biochem) according to a method recommended by the manufacturer to identify a deleted region. In this way, a plasmid pXXN7, in which base pairs from the −1060th position to the −361th position including an upstream regulatory sequence have been deleted, was obtained. Note, the numbering of the nucleotide position was determined by taking "A" of the start codon ATG of GAPDH gene coding region as the position 1.

The plasmid pXXN7 was digested with HindIII to obtain a 3 kb DNA fragment. This fragment was circularized with the following linker using a T4 DNA ligase.

Linker sequence
AGCTTGATATCAAGATCT
ACTATAGTTCTAGATCGA (SEQ ID. No. 4)

The reaction mixture was used to transform E. coli XL1-Blue, and the resulting ampicillin resistant colonies were tested to select colonies having the inserted linker. A single-stranded DNA was prepared from each colony and sequenced using a Sequenase sequencing kit according to a method recommended by the manufacturer to select a plasmid in which the linker has been inserted in the correct orientation, which plasmid was designated as pXXN7L.

A plasmid pJDB-NeoD-ATE for the test of the regulatory sequence was digested with HindIII and XhoI, and a 7 kb fragment was isolated by agarose gel electrophoresis. Note the construction process for pJDB-NeoD-ATE is described in Japanese Patent Application No. 1-41604 (Japanese Unexamined Patent Publication (Kokai) No. 2-222689). This fragment was isolated by a GeneClean kit (BI0101). On the other hand, pXXN7L was digested with HindIII and XhoI, and a 0.4 kb fragment was separated by agarose gel electrophoresis and isolated by a GeneClean kit. 20 ng of the fragment derived from pJDB-NeoD-ATE and 100 ng of the fragment derived from pXXN7 were circularized using a T4 ligase, and the circularized DNA was used to transform E. coli SCS1. The DNA of the resulting ampicillin resistant colonies was tested to select a clone in which the 0.4 kb fragment of pXXN7 has been inserted into pJDB-NeoD-ATE. In this way, a plasmid pXXN7L-NeoD-ATE for the test of the upstream regulatory sequence was obtained. Escherichia coli SCS1/pXXN7L-NeoD-ATE containing the plasmid pXXN7L-NeoD-ATE was deposited with the Fermentation Research Institute of the Agency of Industrial Science and Technology, 1-3 Higashi 1-chome, Tsukuba-shi, Ibaraki, Japan, on Aug. 24, 1990, as FERM P-11681, and transferred to an international deposition under the Budapest Treaty on Aug. 20, 1991, as FERM BP-3518.

EXAMPLE 2

Construction of E. coli Chromosomal DNA Library Using Plasmid pXXN7L-NeoD-ATE for Test of Upstream Regulatory Sequence First, 12.2 tg of the chromosome of E. coli SCS1 was completely digested with 40 units of Sau3AI at 37° C. for 5 hours. The resulting fragment was recovered by phenol extraction and ethanol precipitation. On the other hand, plasmid pXXN7L-NeoD-ATE was completely digested with BglII, dephosphorylated by bovine intestinal alkaline phosphatase, and recovered by phenol extraction and ethanol precipitation. 100 ng of the Sau3AI fragment thus obtained and 50 ng of BglII fragment were circularized using T4 DNA ligase, and the reaction mixture was used to transform E. coli SCS1 to obtain $1.75 \times 10^5$ ampicillin resistant strains. These strains were mixed, cultured, and plasmid DNAs were recovered to obtain a Sau3AI DNA library.

48.8 µg of the chromosomal DNA of E. coli SCS1 was reacted in 500 µl of 50 mM Tris-HCl (pH 7.5), 10 mM $MnCl_2$, and 0.8 ng DNaseI at 37° C. for 10 minutes. 50 µl of 0.5 M EDTA was added thereon to terminate the reaction. DNA was recovered by phenol extraction and ethanol precipitation and treated with mungbean nuclease. DNA was recovered by phenol extraction and ethanol precipitation and dissolved in 170 µl of TE. To the solution were added 20 µl of 10×E. coli DNA ligase buffer (0.2 M Tris-HCl, pH 7.5, 40 mM $MgCl_2$, 100 mM $(NH_4)_2SO_4$, 1 M KCl and 10 mM β-NAD), and the reaction was carried out at 14° C. for 2 hours. 2 units of DNA polymerase I and 20 µl of 1 mM nucleotide mixture (1 mM dATP, 1 mM dTTP, 1 mM dGTP, 1 mM dCTP) were added to the reaction mixture, which was then reacted at 14° C. for 2 hours and then at room temperature for one hour. After phenol/chloroform extraction, DNA was recovered by ethanol precipitation. The recovered DNA was dissolved in 10 µl of TE, and the DNA concentration was determined. 11.8 µg of DNA was recovered.

All the DNA was ligated with BglII linker using T4 DNA ligase in 36 µl of solution. After inactivation of the enzyme, the DNA was completely digested by adding 4 µl 1M NaCl and 50 units of BglII. The reaction mixture was gel-filtrated through a Sephacryl S200 (Pharmacia LKB) column (1 ml bed volume), and DNA fraction eluted near a void volume was recovered. 300 ng of this DNA and 50 ng of the BglII fragment of pXXN7-NeoD-ATE treated as described above were circularized using T4 DNA ligase, and the reaction mixture was used to transform E. coli SCS1 resulting in obtaining $1.64 \times 10^4$ ampicillin resistant strains. These strains were mixed, cultured, and plasmid DNA was recovered to obtain a DNaseI DNA library.

EXAMPLE 3

Isolation of Plasmid Containing Upstream Regulatory Sequence from E. coli DNA Library 20 µg of the library DNA was used to transform Saccharomyces cerevisiae AH22 according to a conventional procedure using LiSCN. Transformants were selected on a leucine-free SD agar medium. When colonies grew to 2 mm in diameter, the colonies were transferred to a YPD agar medium containing 8 mg/ml G418 using a Repli Plate (FMC Corp.), and strains further grown on this medium were selected.

The colonies grown were transferred to a fresh medium containing G418 to isolate colonies. Colonies which grew relatively rapidly on this medium were further selected. As a result, SN1 SN2, and SA1 colonies from the Sau 3AI library, as well as DN1 and DN2 colonies from the DNaseI library were obtained. The SN1 and DN2 strains were separately cultured in YPD liquid medium containing G418, and the whole DNA was prepared. The DNA was used to transform E. coli SCS1, and ampicillin resistant colonies were selected.

Plasmid DNA were prepared from the E. coli colonies, and a restriction enzyme map was prepared. By comparing the maps, 5 plasmids such as pSN1-10, pSN1-12, pSN1-15 from SN1 strain, as well as 4 plasmids such as pDN2-18 from DN2 were isolated. Similarly, pSN2-5, pSN2-1, etc. from the SN2 strain; pSAi-1 etc. from SA1; and pDN1-2, pDN1-7 etc. from DN1 were isolated. These plasmids were used to transform *Saccharomyces cerevisiae* AH22, and transformants were selected on a leucine-free SD agar medium. The formed colonies were transferred onto a YPD medium containing 8 mg/ml G418 to test whether they can grow on that medium. As a result, the yeast strain transformed with pDN2-18 derived from the DN2 strain, or with pSN1-10, pSN1-12 or pSN1-15 derived from the SN1 strain was resistant to G418. Similarly, a yeast strain transformed with plasmid derived from a SN2, SA1, or DN strain acquired resistance to G418.

Figure 2:
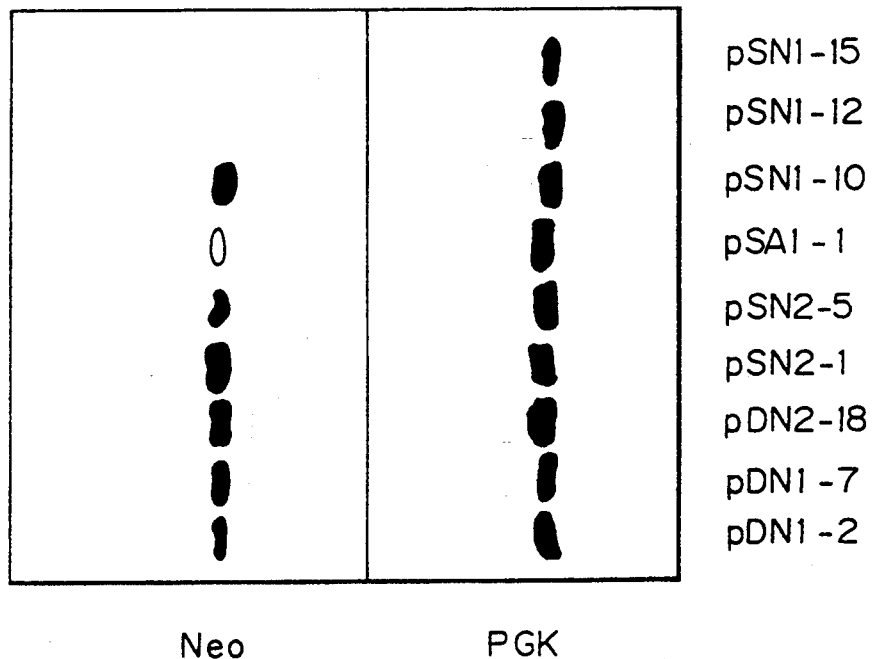
FIG. 2 shows a result of hybridization of a Neo gene or PGK gene probe with mRNA derived from various DNA fragments obtained from the *E. coli* chromosome.

The yeast strains whose G418 resistance was confirmed were cultured in a YPD liquid medium containing 0.5 mg/ml G418, and RNA was prepared according to a conventional procedure. The RNA thus prepared was analyzed by Northern hybridization. The result is shown in FIG. 2. From this result, it is clear that transformant by pDN2-18 and transformant by pSN1-10 efficiently expressed NeoD mRNA.

Since pXXN7L-NeoD-ATE per se cannot provide G418 resistance to yeast, and NeoD mRNA from the transformant by this plasmid was not detected by Northern hybridization, it is clear that the resistance to G418 was provided by pDN2-18 and pSN1-10. Namely, it is believed that *E. coli* chromosomal DNA fragments in pDN2-18 and pSN1-10 have an upstream regulatory sequence. As described above plasmids pSN1-10 and pDN2-18 having an upstream regulatory sequence were obtained.

*Escherichia coli* SCS1/pSN1-10 containing plasmid pSN1-10 was deposited with the Fermentation Research Institute of the Agency of Industrial Science and Technology, 1-3 Higashi 1-chome, Tsukuba-shi, Ibaraki, Japan, on Aug. 24, 1990 as FERM P-11680, and transferred to international deposition under the Budapest Treaty on Aug. 20, 1991, as FERM BP-3517. Similarly, *Escherichia coli* SCS1/pDN2-18 containing plasmid pDN2-18 was deposited on Aug. 24, 1990 as FERM P-11679, and transferred to international deposition under the Budapest Treaty on Aug. 20, 1991, as FERM BP-3516.

EXAMPLE 4

Sequencing of *E. coli* Chromosomal DNA inserted in pSN1-10 and pDN2-18

The plasmid pSN1-10 was digested with HindIII and XhoI to obtain a 0.65 kb DNA fragment containing an *E. coli* DNA fragment and GAPDH promoter. 50 ng of this fragment and 20 ng of pT3T7U18-X (Reference Example 3) which had been digested with HindIII and XhoI were circularized with T4 DNA ligase. The reaction mixture was used to transform *E. coli* XL1-blue to obtain ampicillin resistant colonies. A single-stranded DNA was prepared from a colony and sequenced. A nucleotide sequence of the *E. coli* DNA fragment portion is shown in FIG. 3 and SEQ ID NO:1. It was confirmed that this DNA fragment was derived from *E. coli* by the fact that this fragment hybridises only with *E. coli* chromosomal DNA but not with yeast chromosomal DNA in Southern hybridization using the fragment as a probe. In addition, since no sequence the same as the above nucleotide sequence was found in a gene bank (GENBANK; R58.0), the above-mentioned DNA fragment is novel.

On the other hand, pDN2-18 was similarly analyzed. The pDN2-18 was digested with HindIII and XhoI to obtain a 0.65 kb fragment containing *E. coli* DNA fragment and GAPDH promoter. 50 ng of this fragment and 20 ng of pT3T7U18-X which had been digested with HindIII and XhoI were circularized with T4 DNA ligase. The reaction mixture was used to transform *E. coli* XL1-blue, and ampicillin resistant colonies were obtained. Note the process for construction of the plasmid pT3T7U18-X was described in Reference Example 3. A single-stranded DNA was prepared from a colony and sequenced. A nucleotide sequence of the *E. coli* DNA fragment portion is shown in FIG. 4 and SEQ ID NO:2. It was confirmed that this DNA fragment was derived from *E. coli* by the fact that this fragment hybridises only with *E. coli* chromosomal DNA but not with yeast chromosomal DNA in Southern hybridization using the fragment as a probe. In addition, since no sequence the same as the above nucleotide sequence was found in a gene bank (GENBANK; R58.0), the above-mentioned DNA fragment is novel.

EXAMPLE 5

Figure 5A:
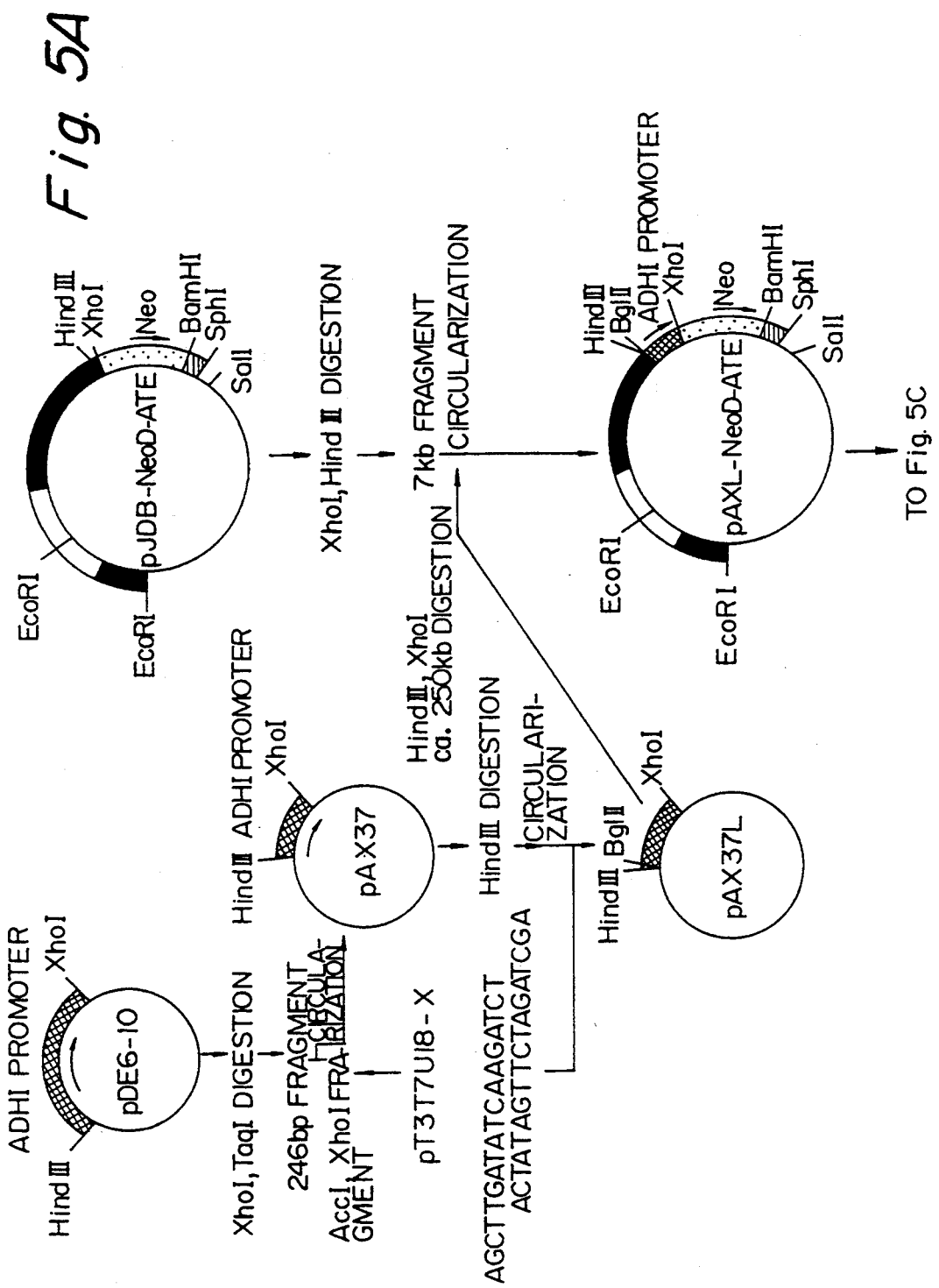
Figure 5B:
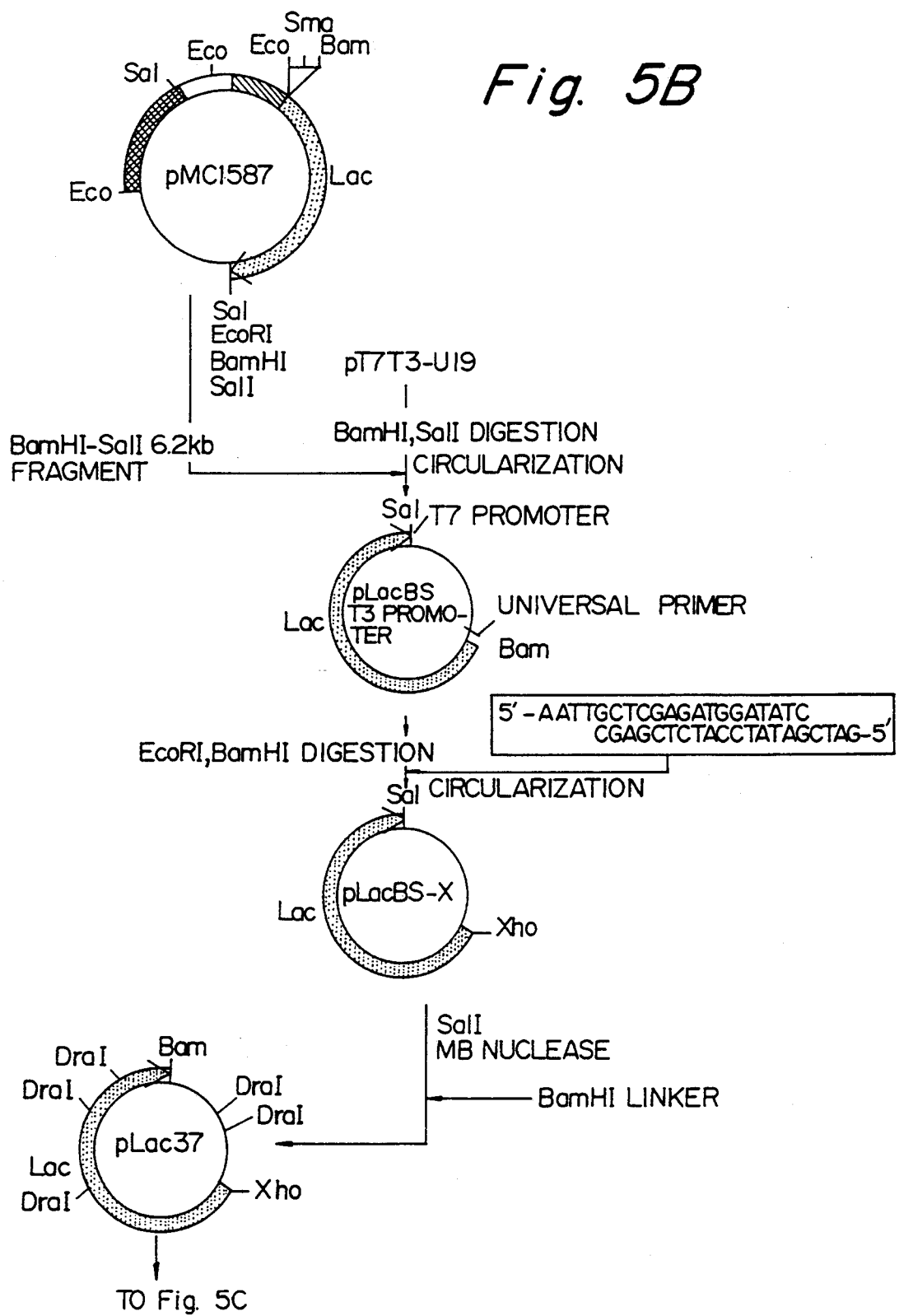

Confirmation of Function as Upstream Regulatory Sequence and Determination of Functional Regions 1) Construction of Test Plasmid pAXL-LacZC-ATE (FIGS. 5A and B)

A test plasmid pAXL-LacZC-ATE for testing the function of an upstream regulatory sequence was constructed as follow. Plasmid pDE6-10 (Xho) (Japanese Unexamined Patent Publication (Kokai) No. 2-117384) (FERM P-10311) (FERM BP-2589) was digested with TaqI and XhoI to obtain a 246 bp fragment. This fragment and pT3T7U18-X digested with AccI and XhoI were circularized with T4 DNA ligase to construct pAX-37. The plasmid pAX37 was digested with HindIII to obtain a 3 kb fragment. This fragment was circularized with a BglII linker of the following sequence:

```
AGCTTGATATCAAGATCT
    ACTATAGTTCTAGATCGA (SEQ ID. No. 4)
``` using T4 DNA ligase.

The reaction mixture was used to transform *E. coli* LX1-Blue to obtain ampicillin resistant colonies, whose DNA was then analyzed to select colonies carrying plasmid to which the linker had been inserted. Single-stranded DNA was prepared from each colony and sequenced using a Sequenase Sequencing kit according to a procedure recommended by the manufacturer to select a plasmid in which the linker had been inserted in the correct orientation. The selected plasmid was designated as pAX-37L. The plasmid pAX-37L was digested with HindIII and XhoI to obtain a fragment of about 250 bp, which was then circularized with a fragment of about 7 kb obtained by digesting pJDB-NeoD-ATE by HindIII and XhoI to obtain pAXL-NeoD-ATE.

On the other hand, plasmid pMC1587 (Method in Enzymology, 100, 293-308, 1983) was digested with EcoR1, BamH1 and SalI to obtain a 6.2 kb BamH1-SalI fragment. This fragment was circularized with pT7T3U19 (Pharmacia) cleaved with BamHI and SalI using T4 DNA ligase to obtain plasmid pLacBS. The DNA fragment obtained by digesting the plasmid pLacBS with EcoRI and BamHI was circularized with the following linker:

```
AATTGCTCGAGATGGATATC
    CGAGCTCTACCTATAGCTAG (SEQ ID. No. 5)
``` by T4 DNA ligase to obtain plasmid pLacBS-X.

This plasmid pLacBS-X was cleaved with XhoI and DraI to obtain a 3.2 kb DNA fragment containing LacZ gene. This fragment was ligated with pT7T3U18 (Pharmacia) cleaved with SmaI and XhoI by T4 DNA ligase to obtain pLacZC-37. The plasmid pLacZC-37 was cleaved with DraI, XhoI and BamHI to obtain a 3.2 kb fragment, which was then ligated using T4 DNA ligase with a 7 kb fragment obtained by cleaving pAXL-NeoD-ATE with XhoI and BamHI to obtain pAXL-Lac ZC-ATE.

2) Test of Function and Determination of Functional Regions

As shown in FIG. 3 and SEQ ID NO:1, pSNl-10 has a DNA fragment of 255 bp derived from the *E. coli*-chromosome. This fragment consists of three Sau3AI fragments of 58 bp, 28 bp and 164 bp respectively. To determine a DNA fragment among three Sau3AI fragments having upstream activating function, each fragment was inserted into a BglII site in pAXL-LacZC-ATE, a resulting plasmid was used to transform yeast cells, and the β-galactosidase activity provided by the transformant was measured. Next, the above procedure was described in more detail.

A plasmid constructed for sequencing containing a HindIII - XhoI fragment of pSNl-10 was cleaved with Sau3AI to obtain fragments of 58, 28 and 164 bp respectively. On the other hand, the plasmid pAXL-LacZC-ATE was digested with BglII, dephosphorylated with bovine intestinal alkaline phosphatase, and recovered by phenol extraction and ethanol precipitation. The Sau3AI fragment thus obtained was ligated with a BglII fragment of pAXL-LacZC-ATE using T4 DNA ligase to obtain pSNl-10 (58), pSNl-10 (164), and pSN1-10 (28). These plasmids contain Sau3AI fragments of 58 bp, 164 bp, and 28 bp respectively. These plasmids were used to transform *Saccharomyces cerevisiae* DC5, and transformants were selected on leucine-free SD agar medium.

The transformants thus obtained were separately cultured in 5 ml of leucine-free SD liquid medium at 30° C. for 2 days. After culturing, the culture broth was centrifuged to collect the cultured cells which were then re-suspended in 100 μl of Z buffer (8.55 g Na₂HPO₄·7H₂O, 2.75 g NaH₂PO₄·H₂O, 0.375 g KCl, 0.123 g MgSO₄·7H₂O, 1.35 ml 2-mercaptoethanol, dissolved in 1 l water). To the suspension was added 100 μl of glass beads (0.4 mm diameter), and vortex-mixing was carried out. After adding 100 μl of Z buffer thereon and mixing gently, the suspension was centrifuged to obtain the supernatant as a cell extract.

The cell extract was added to 1 ml of Z buffer, and 100 μl of 4 mg/ml o-nitrophenyl-γ-D-galactopyranoside solution was added thereon. After mixing, a reaction was carried out at 28° C. After an appropriate time, 250 μl of 1 M sodium carbonate solution was added to terminate the reaction, and the absorbance of the reaction mixture was measured at 420 nm (OD420). The protein concentration of the cell extract was determined using a protein assay solution (Bio-Rad). The activity of β-galactosidase was calculated as follow.

$$\text{Activity} = \frac{OD420 \times 380}{\substack{\text{Reaction} \\ \text{time at} \\ 28° \text{C. (min)}} \times \substack{\text{Amount of} \\ \text{protein used in} \\ \text{reaction (mg)}}}$$

Figure 6:
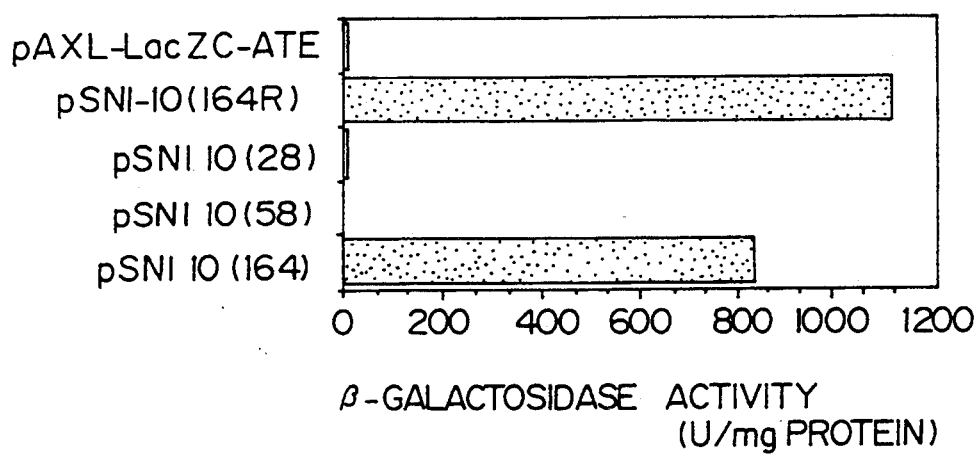
FIG. 6 is a graph comparing the upstream activating actions of three partial sequences in the SN1-10 shown in FIG. 3 and SEQ ID NO:1.

The calculated activities are shown in FIG. 6. The figure shows that the fragment of 164 bp has an upstream activating sequence activity.

It was found by sequencing that pSNl-10 (164) has the UAS inserted in the same orientation relating to the TATA sequence as in pSNl-10. Therefore, a plasmid having the UAS inserted in the reverse orientation relating to the TATA sequence was constructed and tested for upstream activating sequence activity. As seen from FIG. 6, a transformant transformed with plasmid pSNl-10 (164R) in which the upstream activating sequence was inserted in the reverse orientation relative to the TATA sequence produced β-galactosidase. Namely, the 164 bp fragment has a property characteristic to an upstream activating sequence in that a sequence inserted in the reverse orientation does not lose its activity.

Figure 7:
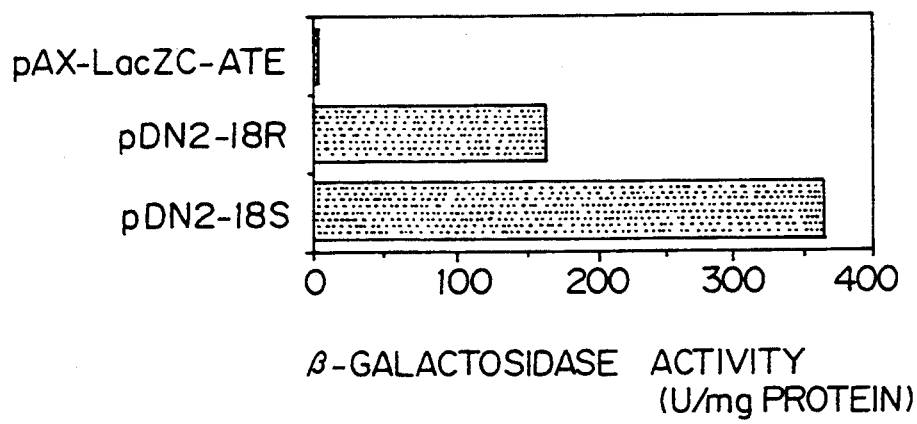
FIG. 7 is a graph showing that the upstream regulatory sequence inserted in either the same (S) or the reverse (R) orientation relating to TATA sequence as in pSN1-10 exhibits an upstream activating action.

On the other hand, plasmid pDN2–18 contained a 153 bp DNA fragment of *E. coli* chromosomal DNA origin, flanked with BglII linkers. This BglII fragment was obtained by cleaving the plasmid pDN2-18 with BglII. This fragment was ligated with an alkaline phosphotase-treated BglII fragment of pAXL-LacZC-ATE using T4 DNA ligase to obtain two plasmids having the upstream activating sequence inserted in different orientations relative to the TATA sequence. A plasmid having the upstream activating sequence inserted in the same orientation as pDN2-18 was designated as pDN2-18S, and that having the upstream activating sequence inserted in the reverse orientation was designated as pDN2-18R. These plasmids were used to transform *Sacchromyces cerevisiae* DC5, and β-galactosidase activity in the cytoplasm of the transformants were measured. As seen from FIG. 7, the activity was detected regardless of the orientation of the upstream activating sequence inserted relative to the TATA sequence. This confirms that the DN2-18 fragment has a property characteristic to upstream activating sequence.

EXAMPLE 6

Construction of Hybrid Upstream Activating Sequence and Test of its Function

Figure 10A:
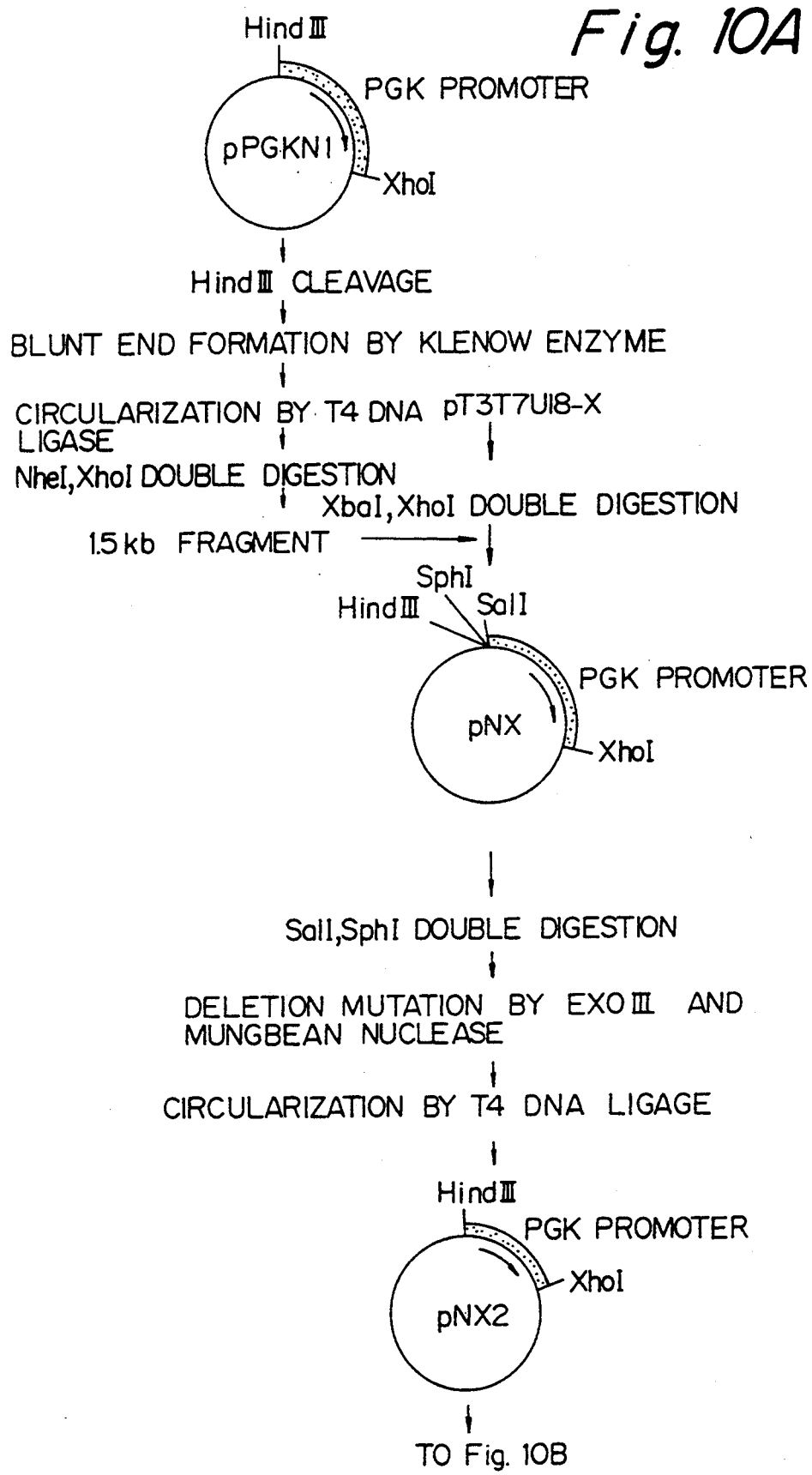
Figure 11A:
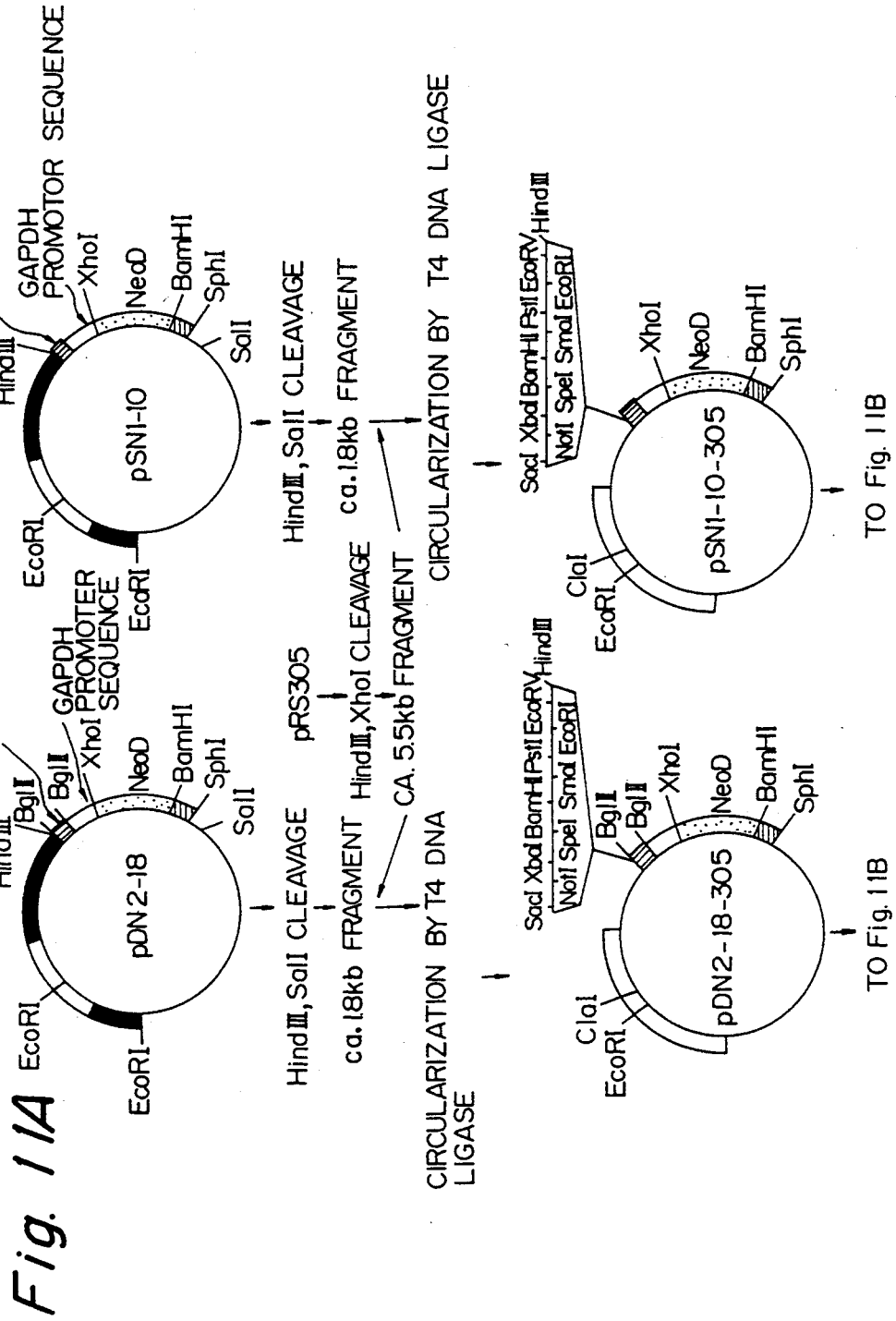
FIGS. 11A and 11B show a process for construction of plasmids pDN2-18-HSA and pDN1-10-HSA.
Figure 11B:
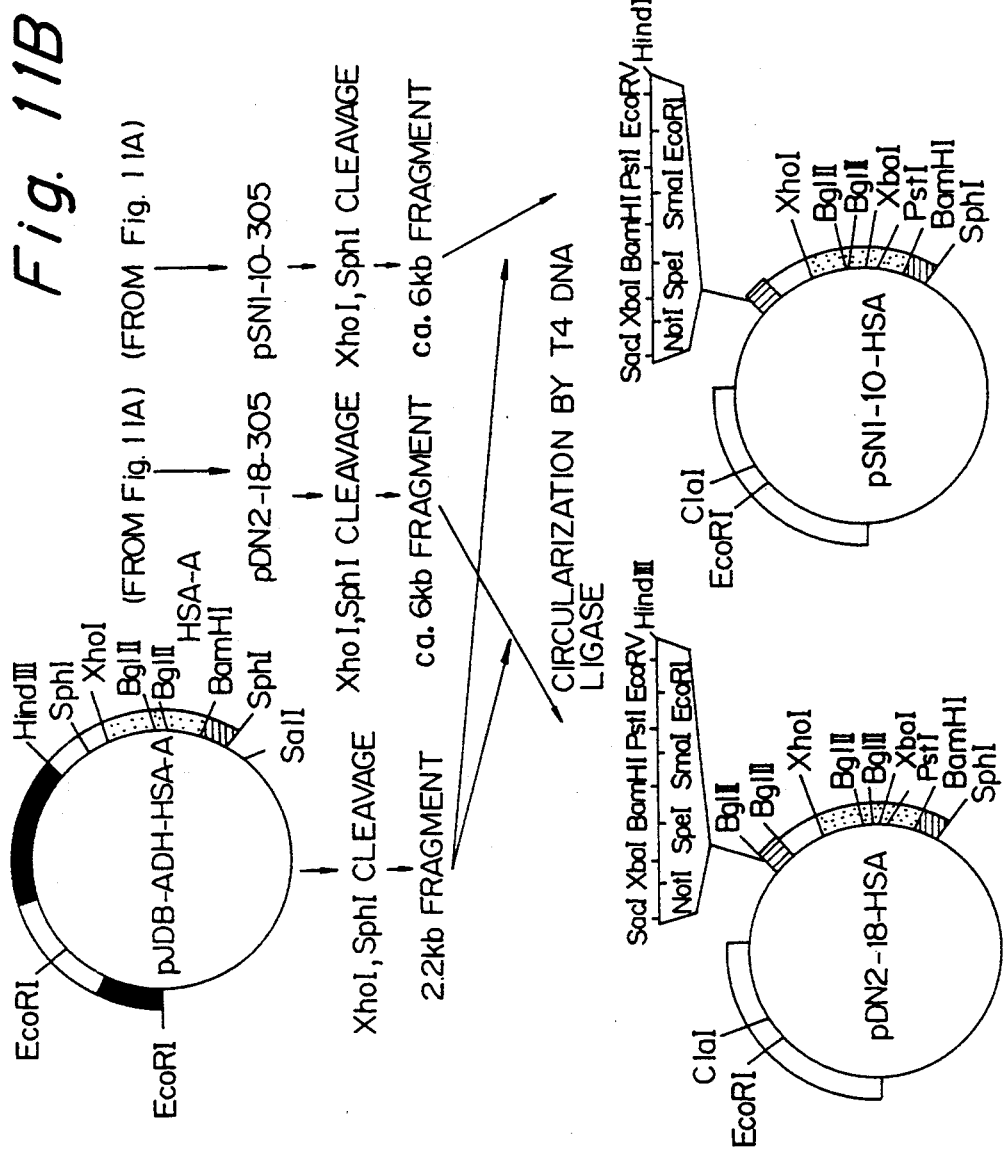

1) Isolation of Upstream Activating Sequence Region of PGK Gene and Insertion Thereof into Test Plasmid (FIGS. 10A and B).

Plasmid pPGKN1 containing a promoter region of yeast PGK gene (prepared as described in Reference Example 1) was cleaved with HindIII, blunt-ended and self-ligated. The resulting plasmid was cleaved with NheI and XhoI to obtain a fragment of about 1.5 kb containing a promoter. This fragment was ligated with pT3T7U18-X cleaved with XbaI and XhoI to obtain plasmid pNX. This plasmid was cleaved with SalI and SphI, subjected to deletion mutation using ExoIII nuclease and mungbean nuclease, and circularized by T4 DNA ligase. The resulting plasmid was used to transform *E. coli* XL1-Blue to obtain ampicillin resistant colonies, whose DNA was then tested to select colonies having deletion-mutated plasmid. Single-stranded DNA was prepared from these colonies and sequenced using a Sequenase Sequencing kit according to a procedure recommended by the manufacturer to identify a deletion region, and pNX2 was obtained.

The plasmid pNX2 was cleaved with HindIII and RsaI to obtain a fragment of about 230 bp. This fragment was ligated with pBluescriptII−KS+(Bgl) cleaved with SmaI and HindIII to obtain plasmid pUAS-PGK. Note, a process for construction of the plasmid pBluescriptII−KS+(Bgl) is described in Reference Example 3. The plasmid pUAS-PGK contains upstream activating sequence of PGK (Kingsman et al., Mol. Cell. Biol. 4335–4343, 1986). The plasmid pUAS-PGK was cleaved with HindIII and BglII to obtain a fragment of about 250 bp. This fragment was ligated with pAXL-LacZC-315 cleaved with HindIII and BglII to obtain pPGK·AX−lacZC.

Figure 8:
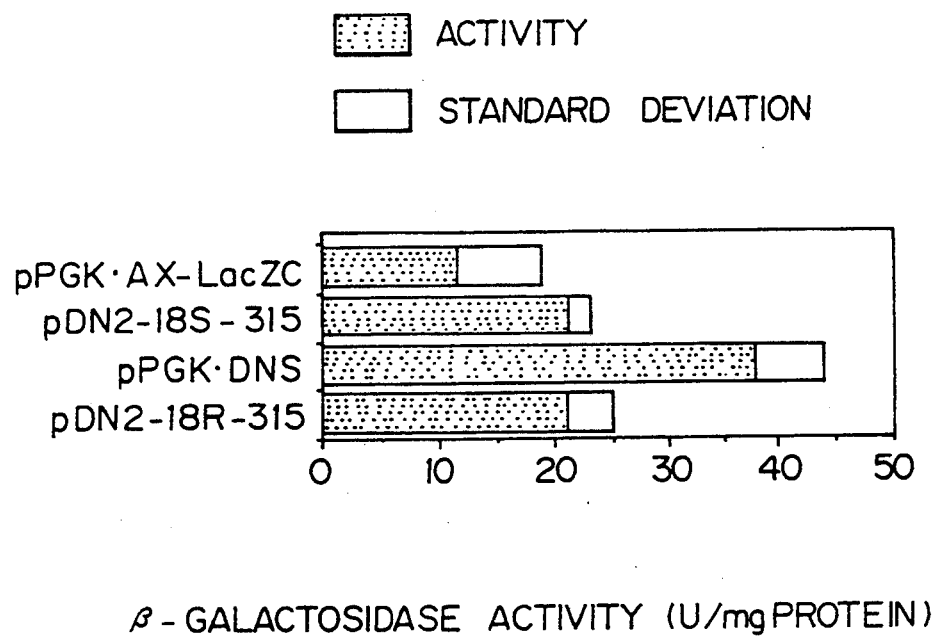
FIG. 8 is a graph showing that a hybrid upstream regulatory sequence of the present invention consisting of an *E. coli* derived upstream regulatory sequence and a yeast promoter, inserted in either the S orientation or the R orientation, exhibits an upstream regulatory action.

2) Test of Hybrid Upstream Activating Sequence FIGS. 8 and 10C)

Plasmid pDN2-18 was cleaved with BglII to obtain a BglII fragment of 153 bp. This fragment was ligated with an alkaline phosphatase-treated BglII fragment of pPGK.AK-LacZC to obtain pPGK-DNS. pPGK·DNS contains a hybrid UAS comprising PGK UAS and DN2-18, and the DN2-18 fragment was inserted in the same orientation relating to the TATA region (see, Example 5, 2)) as confirmed by determination of the nucleotide sequence.

The plasmid was used to transform Saccharomyces. cerevisiae DC5, resulting transformant was cultured, and activity of β-galactosidase produced was measured. The result is shown in FIG. 8. It is clear that a combined upstream activating sequence exhibits an increased activity in comparison with a single upstream activating sequence.

EXAMPLE 7

Expression of Human Serum Albumin Using Hybrid Promoter

Plasmids pDN2-18 and pSN1-10 were cleaved with HindIII and SalI to obtain fragments of about 1.8 kb. Each fragment was ligated with a 5.5 kb DNA fragment prepared by cleaving plasmid pRS305 (Sikorski and Hieter, Genetics 122, 19–27, 1989) with HindIII and SalI, using T4 DNA ligase to obtain pDN2-18-305 and pSN1-10-305, respectively.

Human serum albumin (HSA) expression plasmid pJDB-ADH-HSA-A (Japanese Unexamined Patent Publication (Kokai) No. 2-117384) was cleaved with XhoI and SphI to obtain a fragment of about 2.2 kb containing a HSA-A gene and ADHI transcription terminator. On the other hand, plasmids pDN2-18-305 and pSN1-10-305 were cleaved with XhoI and SphI to obtain fragments of about 6 kb, which were then ligated with the above-mentioned fragment containing a HSA gene using T4 DNA ligase to obtain plasmids pDN2-18-HSA and pSN1-10-HSA for expression of HSA respectively.

Figure 9:
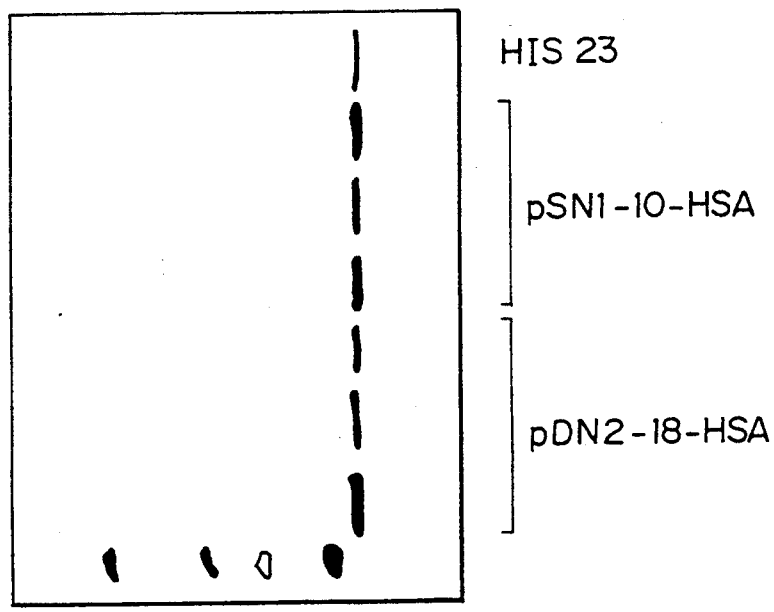
FIG. 9 is a result of electrophoresis showing an expression of human serum albumin under the control of the present hybrid promoter.

Plasmids pDN2-18 and pSN1-10 were used in a linear form prepared by cleavage with ClaI to transform Saccharomyces cerevisiae AH22. Transformants which grew on leucine-free SD agar medium were selected. To test the expression of HSA, the transformants were cultured in SD liquid medium for 2 days, and the culture was inoculated in a YPD liquid medium at a ratio of 1:100. Culturing was carried out for 24 hours, and the amount of HSA secreted in the medium was measured. 0.5 ml of the culture broth was centrifuged to eliminate cells. To the culture supernatant thus obtained, was added the same volume of ethanol, and after mixing the mixture was allowed to stand at 0° C. for one hour to precipitate HSA. The precipitate was collected by centrifugation, and analyzed by SDS-PAGE. As a control, Saccharomyces. cerevisiae HIS23 was prepared by inserting a HSA expressing plasmid into HIS4 locus of the AH22. The result is shown in FIG. 9. As seen from FIG. 9, yeast transformed with plasmid pDN2-15-HSA or pSN1-10-HSA having a hybrid promoter expressed HSA in a larger amount than the control.

REFERENCE EXAMPLE 1

Isolation of Yeast PGK Gene and Construction of Plasmid pPGKN1 Containing Promoter Region of Said Gene Chromosomal DNA of Saccharomyces cerevisiae was partially digested with Sau3AI, and the resulting fragments inserted into a vector EMBL3 (Stratagene) to construct a random phage library. This library was subjected to hybridization with a probe having a nucleotide sequence corresponding to an amino acid sequence from the 9th amino acid to 18th amino acid of coding region of the PGK gene (5'-GTCCAAGATTTGGACTTGAAG-GACAAGCGT-3'SEQ. ID. NO. 6) to obtain a phage clone PGK1 carrying a PGK gene.

PGK1 was digested with HindIII to obtain a 2.95 kb fragment. This fragment was subcloned into a HindIII site of pUC19 to obtain plasmid pUC-PGK. The plasmid pUC-PGK was cleaved with SalI and SacI to obtain a 2 kb fragment containing a promoter region. This fragment was subcloned between SalI and SacI sites of pSV-PL to obtain pSV-PGK. The plasmid pSV-PGK was cleaved with KpnI and SalI to obtain a 2 kb fragment, which was then subcloned between KpnI and SalI of pUC119X to obtain pPGK-PROT.

The pPGK-PROT was cleaved with EcoRV and KpnI and subjected to deletion mutation using ExoIII nuclease and mungbean nuclease. After circularizing with T4 ligase, E. coli XL1-Blue was transformed to obtain ampicillin resistant colonies, whose DNA was then analyzed to select colonies having a deletion mutation. Single-stranded DNA was prepared from these colonies and sequenced using a Sequenase Sequencing kit according to a procedure recommended by the manufacturer, and the deleted region was identified. As a result, pPGKN1 having a promoter sequence deleted up to the −10th nucleotide taking "A" in the translation start codon ATG of PGK gene as "1" was obtained.

REFERENCE EXAMPLE 2

Construction of Test Plasmid DAXL-LacZC-315 having Centromer Sequence as an Origin of Replication Plasmid pAXL-LacZC-ATE was cleaved with HindIII and SalI to obtain a 3.5 kb fragment. This fragment was subcloned between HindIII and XhoI sites in a multicloning site of centromere plasmid pRS315 (Sikorski and Hieter, Genetics, 12.2, P 19–27, 1989) to obtain plasmid pAXL-LacZC-315.

REFERENCE EXAMPLE 3

Construction of Cloning Vectors pT3T7U18-X and pBluescript II-KS+(Bgl).

Plasmid pT7T3U18 (Pharmacia) was cleaved with EcoRI and re-circularized with a linker having the sequence: 5'-AATTGCTCGAGC (SEQ. ID. NO. 7)

using T4 DNA ligase. The resulting plasmid was used to transform *E. coli* XL1-blue to obtain ampicillin resistant colonies, whose DNA was then analyzed to select a colony having a plasmid which was cleaved with XhoI but not cleaved with EcoRI. The plasmiclin selected colony was designated as pT3T7U18-X.

Plasmid pBluescriptII KS+(Stratagene) was cleaved with XbaI and the reaction mixture was heated at 65° C. for 5 minutes to deactivate the enzyme. A 1 mM nucleotide mixture (1 mM dATP, 1 mM dTTP, 1 mM GTP, 1 mM CTP) was added thereon to make the concentration 50 μM. 50 units of DNA polymerase (Klenow fragment) was added to the reaction mixture, which was then incubated at 37° C. for 15 minutes to make XbaI site a blunt end. The mixture was extracted with phenol/chloroform and DNA was recovered by ethanol precipitation. The resulting fragment was circularized with a BglII linker (5'-p-CAGATCTG), and the resulting plasmid was used to transform *E. coli* XL1-blue to obtain ampicillin resistant colonies. The DNA of the colonies was analyzed, and a plasmid cleaved with BglII but not cleaved with XbaI. This was designated as pBluescript II−KS+(Bgl).

---

We claim:

1. An upstream regulatory sequence from *E. coli*, which upstream regulatory sequence functions in yeast cells, and which is an upstream activating sequence consisting essentially of a nucleotide sequence from the 87th G to the 250th C in SEQ ID NO:1 or the nucleotide sequence shown in SEQ ID NO:2.

2. A hybrid upstream regulatory sequence comprising an upstream regulatory sequence from *E. coli* and a yeast upstream regulatory sequence, which hybrid upstream sequence functions in yeast cells, wherein the yeast upstream regulatory sequence is the upstream regulatory sequence of a promoter selected from the group consisting of GAPDH promoter, PGK promoter, ADHI promoter, PYK promoter, ENO1 promoter, and TPI promoter, and the *E. coli* upstream regulatory sequence is an upstream activating sequence consisting essentially of a nucleotide sequence from the 87th G to the 250th. C in SEQ ID NO:1 or the nucleotide sequence shown in SEQ ID NO:2.

3. A hybrid promoter comprising a TATA region of a yeast promoter and an upstream regulatory sequence from *E. coli*, which hybrid promoter functions in yeast cells, wherein the TATA region of a yeast promoter is the TATA region of a promoter selected from the group consisting of GAPDH promoter, PGK promoter, ADHI promoter, PYK promoter, ENO1 promoter, TPI promoter, and FBA promoter, and the *E. coli* upstream regulatory sequence is an upstream activating sequence consisting essentially of a nucleotide sequence from the 87th G to the 250th C in SEQ ID NO: 1 or a nucleotide sequence shown in SEQ ID NO:2.

4. A hybrid promoter comprising a yeast promoter and an upstream regulatory sequence from *E. coli* which hybrid promoter functions in yeast cells, wherein the yeast promoter is selected from the group consisting of the GAPDH promoter, PGK promoter, ADHI promoter, PYK promoter, ENO1 promoter, TPI promoter, and FBA promoter, and the *E. coli* upstream regulatory sequence is an upstream activating sequence consisting essentially of a nucleotide sequence from the 87th G to the 250th C in SEQ ID NO: 1 or a nucleotide sequence shown in SEQ ID NO:2.

* * * * *